United States Patent [19]

Lattore et al.

[11] Patent Number: 4,471,054

[45] Date of Patent: Sep. 11, 1984

[54] PROCESS FOR INACTIVATING FOOT-AND-MOUTH DISEASE VIRUS

[75] Inventors: José L. Lattore; Claudio Denoya; Eduardo Scodeller; César Vásquez; Mario Lebendiker; María S. Dubra; Oscar Crespo, all of Buenos Aires, Argentina

[73] Assignee: Consejo Nacional de Investigaciones Cientificas y Technicas, Argentina

[21] Appl. No.: 324,626

[22] Filed: Nov. 24, 1981

[30] Foreign Application Priority Data

Nov. 25, 1980 [AR] Argentina .............................. 283.355

[51] Int. Cl.³ .............................................. C12N 7/06
[52] U.S. Cl. ..................................... 435/238; 424/89
[58] Field of Search ......................... 424/127, 153, 89; 435/238

[56] References Cited

PUBLICATIONS

Ravilov et al.—Chem. Abst., vol. 91, (1979), p. 102,786g.
Engelbrecht et al.—Chem. Abst., vol. 93, (1980), p. 180,178r.

Primary Examiner—Sam Rosen
Attorney, Agent, or Firm—Scully, Scott, Murphy & Presser

[57] ABSTRACT

A process for inactivating foot-and-mouth disease virus by incubating such virus in the presence of soluble ammonium or Group IA salts and recovering the inactivated and stable virus.

5 Claims, 6 Drawing Figures $C_3$ RESENDE-KINETICS RESIDUAL ACTIVITY AFTER INACTIVATION THE EFFECT OF MONO AND BIVALENT CATIONS ON
THE ACTIVITY OF THE FMDV ENDORIBONUCLEASE

FIG.6

PROCESS FOR INACTIVATING FOOT-AND-MOUTH DISEASE VIRUS

The present invention relates to a new process for inactivating foot-and-mouth disease virus, based on the specific activation of an endonuclease contained in said viruses, which is capable of degrading the RNA responsible for viral replication. When, by degradation of the genomic RNA, the virus is rendered incapable of replication, it is quickly inactivated and is therefore non-infective, thus becoming a suitable material for preparing a foot-and-mouth disease vaccine substantially free from residual infective or toxic effects and possessing a high antigenic activity.

The process of the present invention affords the possibility of replacing traditional methods of inactivation, based on the use of formaldehyde, AEI (acetylethyleneimine) or BEI (binary ethyleneimine) as inactivant agents by means of the application of other agents which do not alter the capacity of the proteins in the viral capsid or the structure of the virus.

BACKGROUND OF THE INVENTION

The foot-and-mouth disease virus, a member of the picornavirus family, is composed by a single stranded RNA sorrounded by a protein capsid. This capsid contains 60 copies of each of the main structural polypeptides $VP_1$, $VP_1$, $VP_3$ and $VP_4$.

During the process of inactivation to degrade the genomic RNA and inhibit the infectivity of the virus there occur alterations of the protein structure of the capsid which affect the immunogenicity of the vaccine. Since 1926, formaldehyde has been used as an inactivant for the virus (1) but it is known that formalinized vaccines contain residual infective particles (2,3). AEI (acetylethyleneimine) and BEI (binary ethyleneimine) (4,5) are better inactivants, since the infectivity of the virus is detroyed by a first order reaction. However, some strains of the virus have prooved unstable when treated with these agents, with marked deterioration of antigenicity after the inactivation (6). Also both inactivants are highly toxic.

Research carried out at the Centro de Virología Animal (CEVAN) led to the detection in purified foot-and-mouth disease virions of the existence of an endoribonuclease. This was the first description of the existence of an active enzyme located within a picornavirus (8, 9). This viral endoribonuclease can be activated to fragment specifically the genome, leaving fully intact capsids with immunogenic capacity, suitable for their use as vaccines.

1. VALLEE, H.; CARRE, H., AND RINJARD, J. (1926). Sur l'immunisation antiaphteuse par le virus formalé. Rév. Gén. Méd. Vét. 35, 128.
2. MOOSBRUGGER, G. A. (1948). Recherches expérimentales sur la fievre aphteuse. *Schweiz. Arch. Tierheilk.* 90, 176.
3. SCHNEIDER, B. (1955). Zur Infektiositat der Maul- und-Klausen der Absorbant Vakzine. *Mn. Tierheilk.* 7, 81.
4. BROWN, F., HYSLOP, N. Sr. G., CRICK J. and MORROW, A. W. (1963). The use of Acetylethyleneimine in the production of inactivated Foot-and-Mouth disease vaccines. *J. Hyg. Camb.* 61, 337.
5. BAHNEMANN, H. G. (1975). Binary ethyleneimine as an inactivant for Foot-and-Mouth disease virus and its application for vaccine production. *Arch. Virol.* 47, 47.
6. STAPLE, R. F., MORRWO, A. W., and FLETTON, B. V. (1975). The effect of acethyleneimine upon a strain of inactivated FMDV virus stored at 4°. *Arch. Virol.* 47, 331.
7. GIRARD, H. C., BAYRAMOGLU, O., EROL, N. and BURGUT, H. (1977). Inactivation of O, FMDV virus by the binary Ethyleneimine (BEI). *Bull Off. Int. Epiz.* 87, 201.
8. DENOYA, C. D., SCODELLER, E. A., GIMENEZ, B. H., VASQUEZ, C. and LA TORRE, J. L. (1978). Foot-and-Mouth disease virus. (I) Stability of its ribonucleic acid. Virology 84, 230.
9. DENOYA, C. D., SCODELLER, E. A., VASQUEZ, C. and LA TORRE, J. L. Foot-and-mouth disease virus. (II) Endoribonuclease activity within purified virions. Virology 57, 153.

SUMMARY OF THE INVENTION

Experiments in activating the enzyme in the open virion (released by heat and/or pH) were performed and activation by monovalent cations such as ammonium, and potassium at concentrations as low as 100 mM, was found. The addition of bivalent cations such as $Mg^{2+}$ and $Ca^{2+}$ (5 mM) produced greater activation of the enzyme. In the open virion, the maximun amount of activation was obtained with the 100 mM - 5 mM bivalent combination.

It was also found that non-ionic detergents such as Triton X-100, at concentrations of between 0.1 and 0.5%, NP40, BRIJ, Tween, nd other similar substances are other potent activators of the enzyme, particularly in the specific case of the type C foot-and-mouth disease virus. Tests caried out showed that, for example, Triton X-100 is a real "in vitro" activator of viral nuclease. On the other hand, Triton X-100 quickly dissolves virus clusters, permitting a better interaction of these with the ammonium cation. It was evidenced several times by electron microscopy. Similarly, the recovery of virios was substantially greater in multiple tests carried out in the laboratory.

BRIEF DESCRIPTION OF THE DRAWINGS.

FIG. 6 graphically depicts the effect of mono- and bivalent cations on the activity of the FMDV endoribonuclease.

DESCRIPTION OF THE PREFERRED EMBODIMENTS

Investigations were made as to the possibility of producing 140S particle mass with degraded RNA. Three roller bottles containing a monolayer of BHK 21 cells obtained from CEPANZO (Centro Panamericano de Zoonosis, Argentina) were infected at low multiplicity with $A_{24}$ Cruzeiro virus obtained from SELAB. The infection was left overnight; one roller bottle was infected in the presence of $^3$H-uridine, so as to label the virus. The cellular fluids were centrifuged for 15 min. at 12,000 rpm and the supernatant fluids were divided into 5 aliquots of 2.5 ml each. The aliquots were treated as follows:

| A Control | Eagle | 0° 14 hr |
|---|---|---|
| B Control | Eagle, Tris 100 mM, NH$_4$Cl 500 mM (pH 8.5) | 37° 14 hr |
| C Incubated | Eagle, Tris 100 mM, NH$_4$Cl 500 mM, NH (pH 8.5) | 37° 14 hr |
| D Incubated | Eagle, Tris 100 mM, NH$_4$Cl 500 mM (pH 8.5) | 37° 1 hr |
| E Incubated | Eagle, Tris 100 mM, NH$_4$Cl 500 mM, Triton 0.5% (pH 8.5) | 37° 1 hr |

Figure 1:
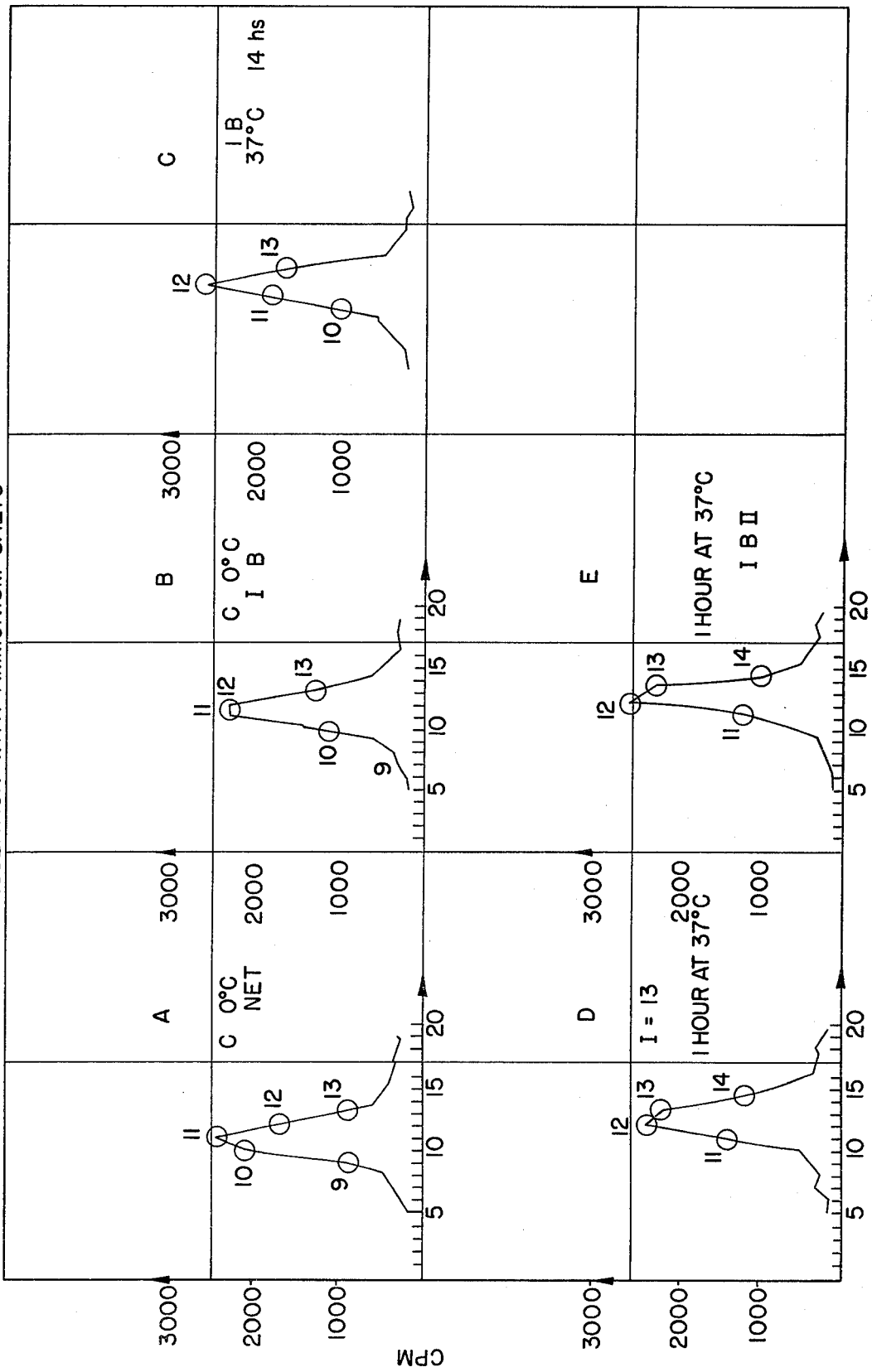
FIG. 1 illustrates the recovery of 14OS virions after incubation with ammonium salts under varying conditions (A–E).
Figure 2:
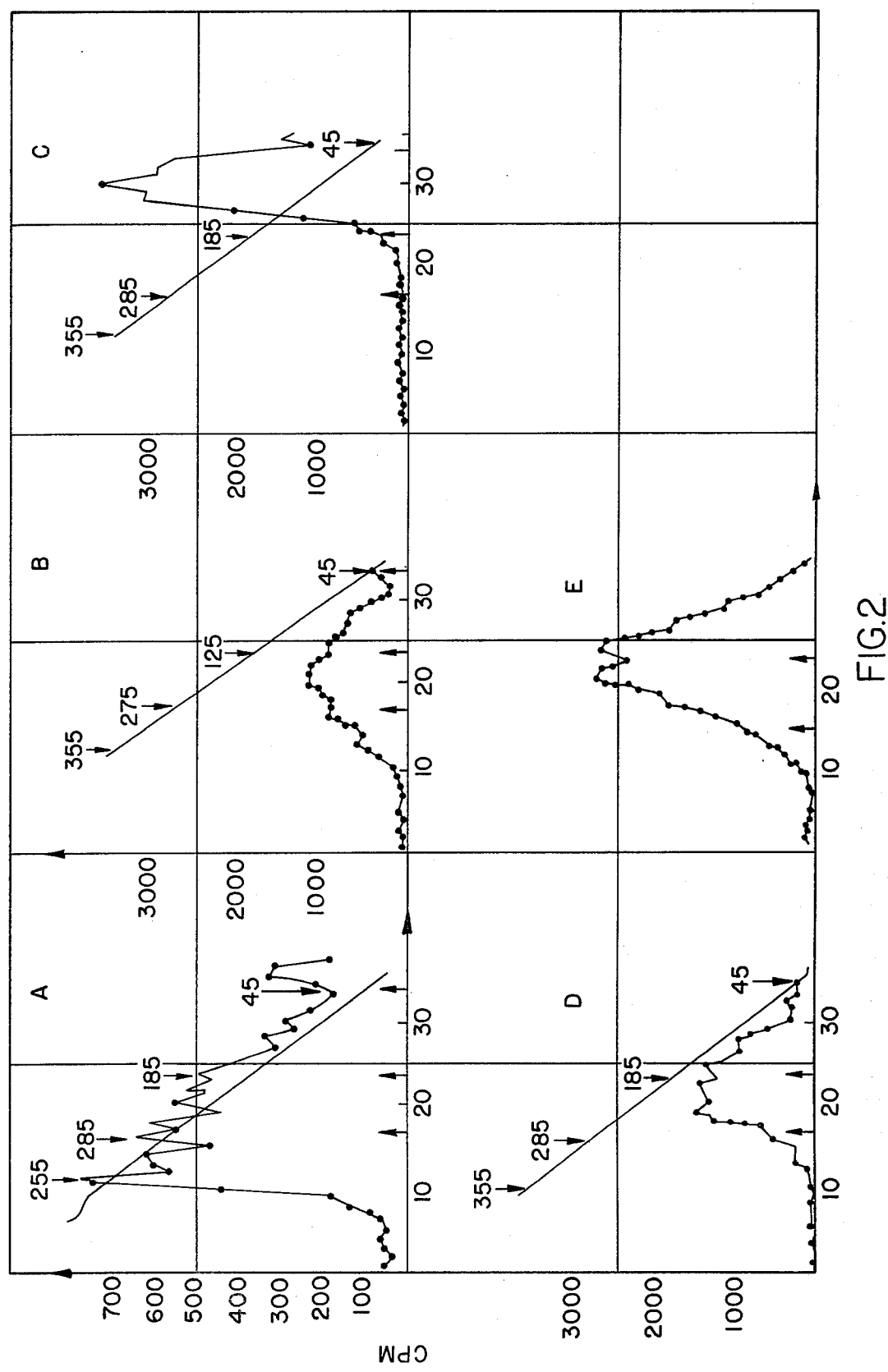
FIG. 2 illustrates the intactness of the genomic RNA extracted from each group of virions (A–E) of FIG. 1.
Figure 3:
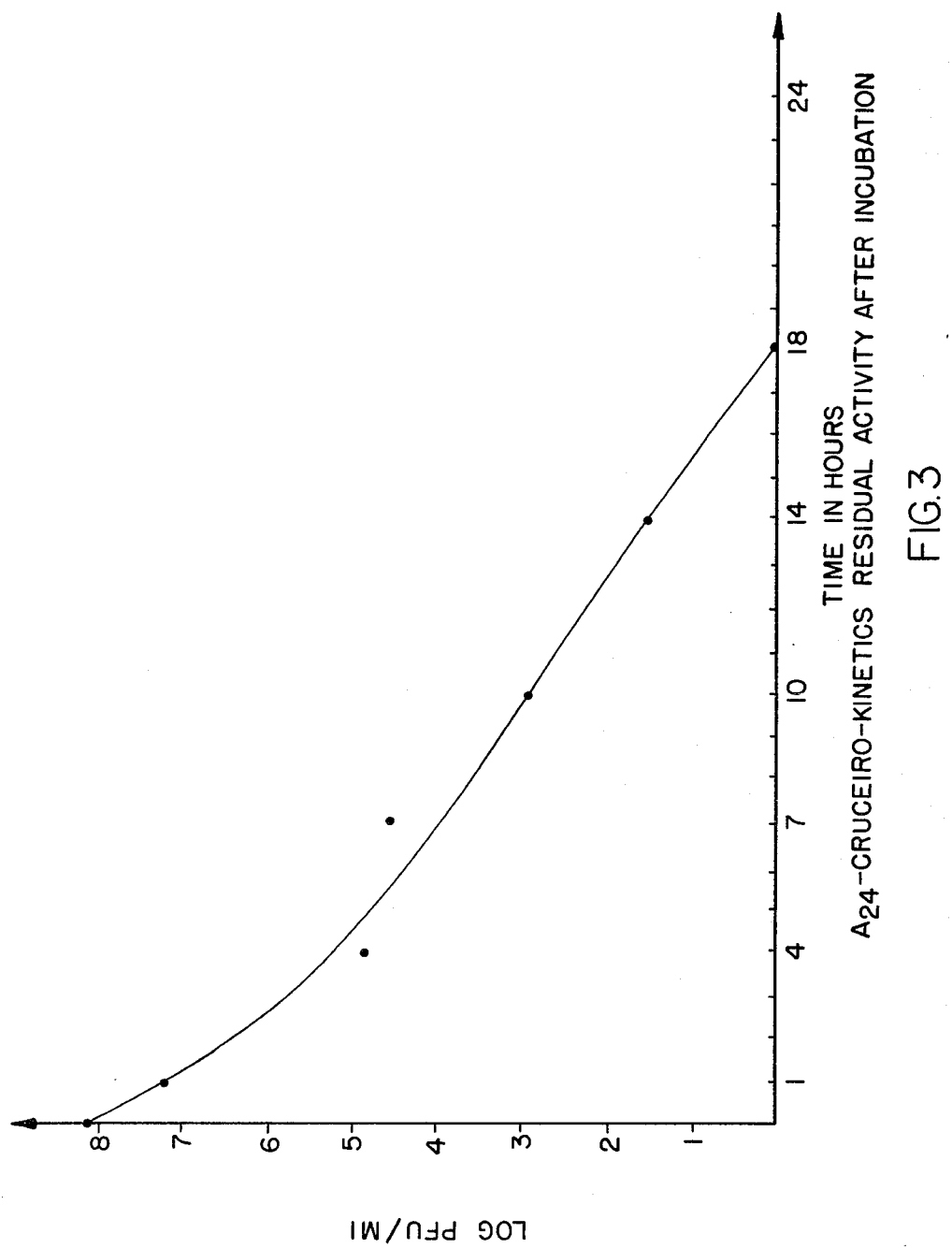
FIG. 3 graphically depicts $A_{24}$ -cruceiro-kinetics residual activity after inactivation.

After the respective treatments, each sample was purified as follows for the purpose of obtaining 140C particles:

Each fraction was brought to 20 mM EDTA (neutralised to pH 7.4) and to 0.2% Sarkosyl, NL 97 (Geigy) and leyered onto 10–30% (w/v) linear sucrose gradient made in NET buffer (100 mM NaCl, 1 mM EDTA, 50 mM Tris-HCl, pH 7.4). The samples were run in an SW27 rotor (Beckman ultracentrifuge) for 3.5 hr at 26,000 rpm and at 2°. The total radioactivity of each aliquot of the gradient was counted in a liquid scintillation counter. The data obtained show that recovery of 140S particles was not significantly affected by the various treatments (FIG. 1) (the experiment was repeated 5 times with like results). The fractions of each gradient containing virus were pooled, brought to 1% (w/v) with SDS and extracted twice with phenol - chloroform at 60°; the extracted RNA was precipitated with alcohol, resuspended in NET buffer +0.1% SDS and analysed in sucrose gradients made in NET-SDS, 10–30% (w/v), and run at 20°, 22,000 rpm, 14 hr 30 min. Nonradioactive ribosomal RNA and 4S were used in each gradient as internal markers. Intense degradation of 35S RNA into fragments of low molecular weight was observed in the virions treated with NH$_4$Cl (FIG. 2).

However, for reasons of sensivity of the methods used, it was not possible to be certain of total absence of infective 35S RNA. It was therefore decided that the biological immunity tests described in Part Three should be undertaken. In addition, the intactness of the viral particles was examined by electron microscopy and the preservation of the immunogenic protein was investigated by analysis of the proteins in polyacrylamide gels (for which purpose the virus was labeled with a mixture of $^3$H amino acids). No differences between control and treated, inactivated virus were observed, demonstrating that the virion would be suitable for further processing into a vaccine.

With intact 140S particles with their RNA degraded, the safety of the virus by biological methods, and the preparation of an experimental vaccine, were investigated.

An important point was the utilisation of biological tests to adjust the inactivation time of the virus. A$_{24}$ Cruzeiro virus originally obtained at SELAB was used. This virus was then closed on BHK monolayer and used in successive passages (approximately 30 passages in BHK monlayer. The virus was produced normally in roller bottles (3.5×10$^8$ cells each) and in all cases the clarified fluid was used for centrifugation for 10 min at 10,000 rpm; the resultant supernatant fluid was then always used. The viruses were plated in petri dishes or on flasks, by conventional techniques.

The main subject of this invention is, therefore, a process ofr inactivating foot-and-mouth disease virus, characterized in that it comprises incubating said virus in the presence of soluble salts selected from among ammonium salts and Group IA salts, as required in the presence of non-ionic detergent and Ca$^{2+}$ or Mg$^{2+}$ in the culture medium where the virus was produced.

EXAMPLE (1) Safety testing by plating on monolayer: A$_{24}$ Cruzeiro virus from one roller bottle was divided into two aliquots of 10 ml each. One was used as control and was kept at 0° for 18 hr. The other aliquot was inactivated by the addition of 100 mM Tris and 500 mM of NH$_4$Cl at pH 8.5 (final pH of the inactivation reaction) and by incubation at 37° for 18 hr. Both viruses were pelleted out at 49,000 rpm in a fixed-angle 50 Ti rotor for 60 min at 4°. The incubation was carried out also in the presence of 0.2% Triton X-100 and MgCl$_2$ 2 mM. The pellets were resuspended in 1 ml (10× the original) of Eagle's medium. The viruses were finally diluted in base 10 and plated.

Figure 4:
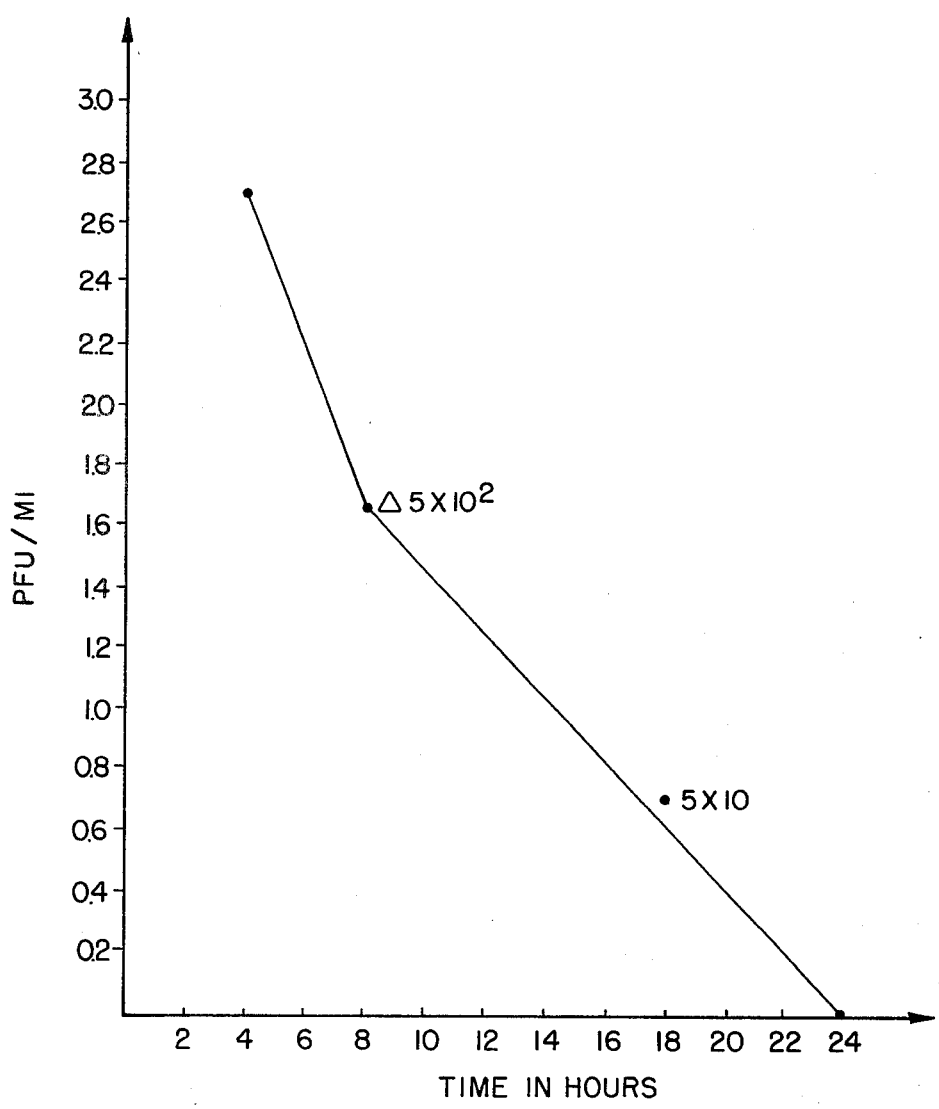
FIG. 4 graphically depicts $C_3$ -resende-kinetics residual activity after inactivation.

Titre of control virus: $1 \times 10^7$ PFU/ml
Titre of inactivated virus: negative at all dilutions
Titre of virus inactivated with Triton X-100+Mg$^{2+}$:
  Negative at all dilutions (2) Inactivation kinetics: A$_{24}$ Cruzeiro (see above) in clarified fluids from 4 roller bottles was pooled and divided into 7 aliquots of 10 ml each. The material was stored at 0° until use. The inactivation times were 1 h, 10 hr, 14 hr, and 18 hr. In all cases, the same inactivation procedure as described above was used (Tris 100 mM, NH$_4$Cl 500 mM, pH 8.5). The inactivations were performed at set intervals so that all the points ended simultaneously. FIG. 4 shows the inactivation curve obtained. This curve was repeated three times but its end points extended to 20, 24, and 26 hr. were repeated five times with negative results. In this case Triton X-100 and Mg$^{2+}$ did not alter the results either.

(3) Safety test in the unweaned mouse: A$_{24}$ Cruzeiro virus (see above) was ued in 5 to 8 day unweaned mice of Rowland breed, obtained from private breeders in Argentina. The virus from one roller bottle was clarified and two aliquots of 5 ml each were separated out. One was used as control and the other was inactivated as stated above for 20 hr in the presence of Triton X-100 and MgCl$_2$.

The inactivated virus was raised to 5 times the concentration by pelleting. The control virus was used direct. Each mouse was injected with 0.125 ml of the virus intraperitoneally (there was no deaths from traumas). Control tests were performed with virus-free Eagle's medium.

| RESULTS | 24 hr I/S | 48 hr I/S | 168 hr I/S |
|---|---|---|---|
| Eagle's medium only 5 mice injected MOTHER A | 5/5 | 5/5 | 5/5 |
| Virus 1 × | 5/5 | 5/0 | — |
| Eagle's medium only 5 mice injected MOTHER B | 5/5 | 5/5 | 5/5 |
| Inactivated virus (5 ×) | 5/5 | 5/5 | 5/5 |

| RESULTS | 24 hr I/S | 48 hr I/S | 168 hr I/S |
|---|---|---|---|
| 5 mice injected | | | |

I = Injected
S = Surviving (4) C$_3$ Resende: It was decided that a wild strain should be studied and C$_3$ Resende virus, which was obtained passed through guinea pigs from SELAB (SENASA) was selected. The virus had undergone 6 passages through guinea pig. At the Centro de Virología Animal it was passed through guinea pig in passages 7, 8 and 9 by conventional techniques. Virus from the 7th passage in guinea pig was adjusted to BHK monolayer in 5 passages (working stock). One aliquot was inactivated as already described for A$_{24}$, but with the addition of 1.0% of Triton X-100 and 2 mM MgCl$_2$, for 24, 26 and 28 hr. The virus was pelleted and concentrated 10×, resuspended in Eagle salts without Triton and plated by a conventional technique.

| Trite of control: | 24 hr | 2.5 × 10$^9$ PFU/ml |
|---|---|---|
| | 26 hr | 3.25 × 10$^9$ PFU/ml |
| | 28 hr | 2.75 × 10$^9$ PFU/ml |

In all cases the dilutions of virus inactivated for 20 hr were negative.

(5) Inactivation Kinetics of C$_3$ Resende virus. Inactivation was performed in Tris-ammonium-Triton buffer at 37° for 4, 8, 18 and 24 hr. with virus from a single viral infection. At the end of the activation the virus was pelleted and resuspended 10× in Eagle's medium and plated.

The titre of the control was upwards of 10$^9$ PEU/ml (FIG. 4). In addition, a single tissue culture test was performed (monolayer Roux 1×10$^8$ cells). Three serial passages were performed and were negative as judged by observation of the cells under an optical microscope.

Figure 5:
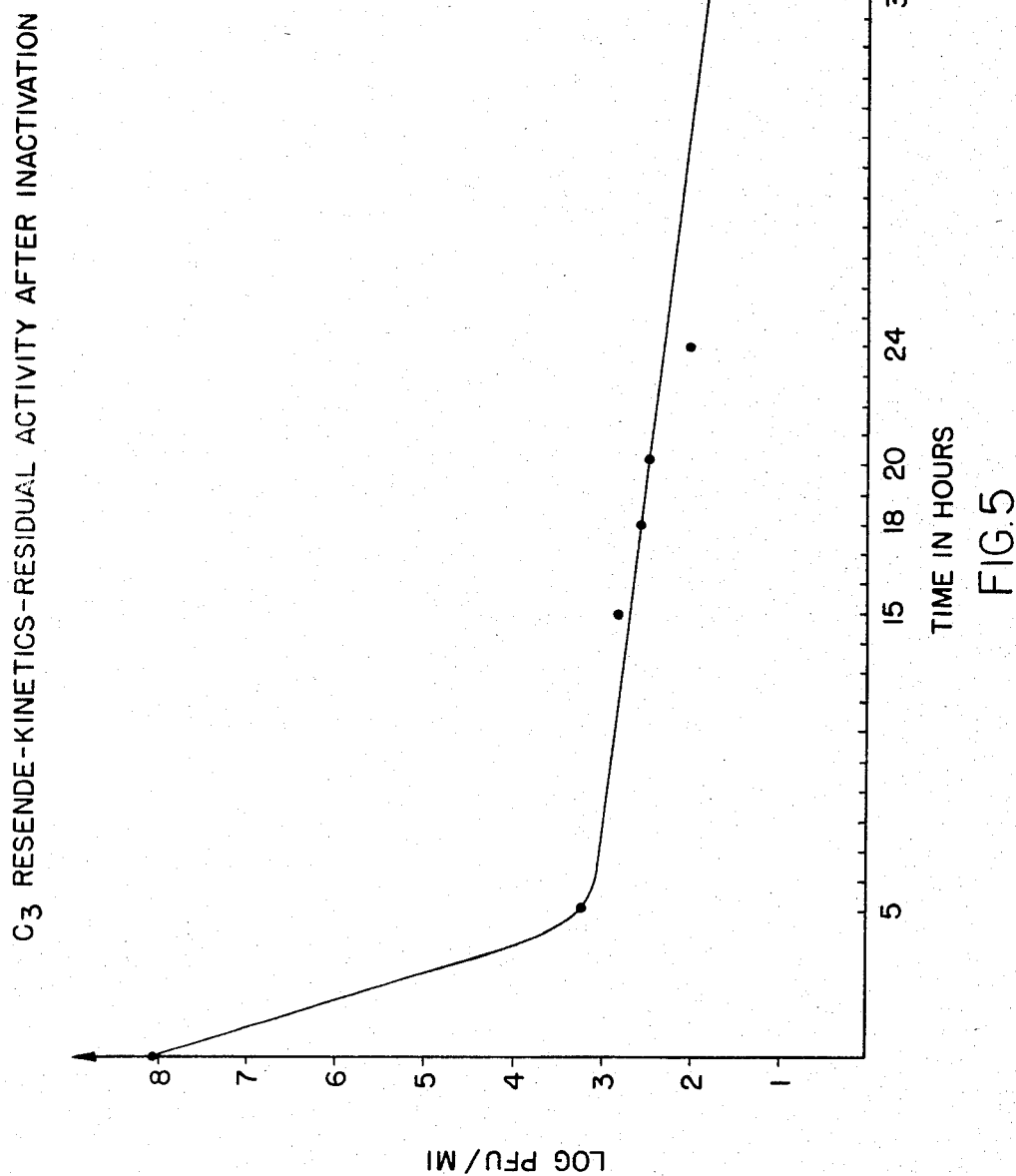
FIG. 5 graphically depicts $C_3$ -resende residual activity after inactivation.

(6) Inactivation of the C$_3$ Resende virus in the absence of Triton X-100. The inactivation shown in FIG. 4 was performed in the presence of Triton X-100. The basis of the utilisation of this non-ionic detergent results upon the fact that the type C viruses tested —i.e. C$_3$ Resende —a re inactivated with kinetics of the second order in the absence of the detergent (FIG. 5). In view of this result, the Centro de Virología Animal standardised its techniques using Triton X-100 on a regular basis in all its subsequent experiments and with a view to obtaining in all cases inactivations tending to zero risks (said FIG. 4 corresponds to the inactivation kinetics (C$_3$ Resende) in Tris-ammonium-Triton-Mg$^{2+}$—*Log PFU/ml vs. residual activity per inactivation*).

(7) The influence of mono and bivalent cations on the "in situ" activation of the viral nuclease is illustrated in FIG. 6, in drawings A-F, in which the variation of $^3$H Uridine CPMX10$^{-2}$ is represented on the basis of the number of polyacrylamide gel fractions.

FIG. 6A corresponds to the readings made on samples of virions broken through heating at 60° C. during 3 minutes, incubated in the presence of ClNa 100 mM (50 mM Tris HCl) thus showing that Na+ does not operate on nuclease. FIG. 6B corresponds to the same test made in the presence of ClNH$_4$ under identical conditions. Here, a greater influence of NH$_4$ is noticed as compared to Na+, in open vibrions, a situation which is repeated in tests of FIGS. 6C and 6D corresponding to the study of the Mg$^{2+}$ influence on open vibrions.

FIGS. 6E and 6F correspond to tests made in entire vibrions. The 6E test refers to the treatment of said virions with ClNH$_4$ according to the present invention. The microscopic observation of the unbroken virions incubated with ClNH$_4$ show a better conservation of the capside, a situation which is repeated with Cs+ and K+, reinforceable by Ca$^{2+}$ and Mg$^{2+}$. (Electronic microscope).

(8) Preparation of an experimental Vaccine. Four roller bottles were infected with C$_3$ Resende (5th passage in BHK monolayer) and a pool of clarified viral suspension was obtained as already described. The pooled material was divided into two aliquots, one as control to obtain the titre of virus and the other for inactivation. The latter aliquot was inactivated with the buffer specified above for 28 hr at 37° and was stored at 0° until use. From this virus inactivated in the presence of Triton X-100 and Mg$^{2+}$ one aliquot was taken for plating tests (after pelleting and resuspension 10 ×) and safety tests in unweaned mice, and the remainder was used to prepare the experimental vaccine.

The vaccine concentration was adjusted to give 3 dosages of faccine: 10 ug per dose, using the colloidal aluminium hydroxide/saponin method (192 ml/12 ml of faccine suspension, 1/1 dose). The dilutions were made with PBS.

Titre of control virus: 2.8×10$^9$ PFU/ml

Plating control of inactivated virus: all dilutions were negative. Safety in unweaned mouse: negative for all the animal inoculated with the inactivated virus.

(9) Potency test: guinea pig 50% infective dose. C$_3$ Resende virus passed 8 times in guinea pig, processed in accordance with SELAB (SENASA) standards, was used. It was calculated that in 50% of the animals the lesion generalised in 5/7 days with 10$^{-4}$ dilution of said suspension of virus.

Groups of guinea pigs were inoculated with the vaccine prepared in accordance with point (8) and according to the following design:

| (A) Negative control: | 7 guinea pigs |
|---|---|
| (B) Challenge control: | 5 guinea pigs |
| (C) 10 ug dose: | 8 guinea pigs |
| (D) 5 ug dose: | 5 guinea pigs |
| (E) 2.5 ug dose: | 5 guinea pigs |

For the first 8 days the guinea pigs were observed for detection of any viral lesions produced by the vaccine, with a negative result for all of them. At 21 days after the vaccination, groups B, C, D and E were challenged with 10−3 dilution of C$_3$ Resende virus passed in guinea pig, 8passage, and by the 7th day generalisation of the virus was observed.

| RESULTS | |
|---|---|
| 10 ug dose: | Protection |
| 5 ug dose: | Protection |
| 2.5 ug dose: | Protection |
| Challenge control | FMDV severe lesions (less than 5 days) |

We claim:
1. A process for inactivating foot-and-mouth disease virus, comprising incubating said virus in the presence of soluble salts selected from among ammonium salts and Group IA salts, maintaining the proteic structure of the intact capside and recovering the completely inactivated and stable viruses.

2. The process according to claim 1 wherein said incubation is done in the presence of a non-ionic detergent.

3. The process according to claims 1 or 2 wherein the culture medium contains $Mg^{2+}$ and $Ca^{2+}$ ions.

4. The process according to claim 1 wherein said Group IA salts are selected from among potassium and cesium salts.

5. The process according to claim 2 wherein said non-ionic detergent is Triton X-100.

* * * * *

UNITED STATES PATENT AND TRADEMARK OFFICE
CERTIFICATE OF CORRECTION

PATENT NO. : 4,471,054
DATED : September 11, 1984
INVENTOR(S) : Jose L. Lattore, et al.

It is certified that error appears in the above-identified patent and that said Letters Patent are hereby corrected as shown below:

ON THE COVER PAGE:

[73] Assignee: Please add --Fundacion para la Educacion, la Ciencia y la Culture, Moreno Buenos Aires, Argentina part insterest --.

Column 1, Line 30, delete the second "$VP_1$" and insert therefor --$VP_2$--.

Column 1, Line 40, delete "detroyed" and insert therefor --destroyed--.

Column 2, Line 32, delete "nd" and insert therefor --and--.

Column 2, Line 35, delete "caried" and insert therefor --carried--.

Column 3, Line 63, delete "closed" and insert therefor --cloned--.

Column 3, Line 65, delete "monlayer" and insert therefor --monolayer--.

Column 4, Line 4, delete "ofr" and insert therefor --for--.

Column 4, Line 30, after "Cruzeiro" insert --virus--.

Column 4, Line 33, delete "h" and insert therefor --hr--.

UNITED STATES PATENT AND TRADEMARK OFFICE
CERTIFICATE OF CORRECTION

PATENT NO. : 4,471,054
DATED : September 11, 1984
INVENTOR(S) : Jose L. Lattore, et al.

It is certified that error appears in the above-identified patent and that said Letters Patent are hereby corrected as shown below:

Column 4, Line 45, delete "ued" and insert therefor --used--.

Column 6, Line 40, delete "(8)" and insert therefor --(6)--.

Column 6, Line 53, delete "10-3" and insert therefor --$10^{-3}$--.

Column 6, Line 54, delete "8passage" and insert therefor --8th passage--.

Column 6, Line 62, delete "severe" and insert therefor --several--.

Signed and Sealed this

Seventeenth Day of December 1985

[SEAL]

Attest:

DONALD J. QUIGG

Attesting Officer

Commissioner of Patents and Trademarks